United States Patent [19]

Smith et al.

[11] 4,448,764
[45] May 15, 1984

[54] DIRECT-ACTING IODINATING REAGENT

[75] Inventors: Paul K. Smith; Dennis C. Klenk, both of Roscoe, Ill.

[73] Assignee: Pierce Chemical Company, Rockford, Ill.

[21] Appl. No.: 395,805

[22] Filed: Jul. 6, 1982

[51] Int. Cl.$^3$ ...................... A61K 43/00; A61K 49/00
[52] U.S. Cl. ..................................... 424/1.1; 252/645; 428/407; 424/9; 521/25
[58] Field of Search ................ 424/1, 9, 1.1; 428/407; 521/25; 252/645

[56] References Cited

U.S. PATENT DOCUMENTS 4,107,283 8/1978 Pratt et al. ............................. 424/1
4,243,652 1/1981 Francis ..................................... 424/1
4,290,965 9/1981 Stöcklin et al. ......................... 424/1

FOREIGN PATENT DOCUMENTS 829634 5/1981 U.S.S.R. .............................. 428/407

OTHER PUBLICATIONS

Maeda et al., Int. J. Appl. Rad. Isotopes, 30 (1979), 713–714, 255–257.
Huh et al., Chem. Abstracts, 82 (1975), #17431g.
Merkushev et al., Chem. Abstracts, 95 (1981) #63162m, (Abstract of USSR #829634).
Kabalka et al., Int. J. Appl. Rad. Isotopes, 33 (1982), 223–224.

Primary Examiner—Christine M. Nucker

[57] ABSTRACT

There is disclosed an effective direct-acting iodinating reagent for biological specimens which, because it is direct, avoids the necessity of having present at the same time both an oxidizing agent and sodium iodide. The reagent is a conjugate of an iodous ion and a water insoluble support. The manner of conjugation is such that the ion is complexed onto the surface of the support but is still free to react with groups in proteins susceptible to iodination and thus be transferred to the biological specimen being iodinated. Apart from the advantage of being direct-acting, the reagent has those desirable attributes which are associated with water insoluble oxidants.

13 Claims, No Drawings

DIRECT-ACTING IODINATING REAGENT

This invention relates to the iodination of biological specimens and, more particularly, to a new iodinating reagent which is useful in directly iodinating biological specimens.

Radioactive labelling, usually with radioactive iodine in the form of the iodous ion (I+), of biological specimens is an important technique in a number of biochemical applications. Such applications include diagnostic procedures based on radioimmunoassay, membrane and cell receptor studies, and conformation studies of proteins and peptides.

Because of the presence of the amino acid tyrosine in most biological specimens and the facile reaction of I+ with the phenolic moiety thereof, radioiodination of the tyrosyl residue is the usual method of choice where radioactive labelling is to be employed. However, because of the extreme volatility of free iodine, the iodous ion (I+) is customarily generated in situ from sodium iodide with the use of an oxidant. N-chloro-4-methyl-benzenesulfonamide, commonly referred to as chloramine-T, has for a number of years been used as the oxidant to mediate iodination reactions. Other oxidants which have been used include the immobilized enzyme, lactoperoxidase, and the compound, 1,3,4,6-tetrachloro-3$\alpha$, 6$\alpha$/ diphenylglycouril("Iodogen", trademark of Pierce Chemical Company). As opposed to chloramine-T, these latter two oxidants are not harsh on the specimen being iodinated and are water insoluble, a feature which permits easy termination of the iodination reaction.

More recently, an improved oxidant has been described in U.S. patent application Ser. No. 311,077, filed Oct. 13, 1981, by Pual K. Smith. The oxidant is in the form of a bead with chloramine groups covalently attached to the bead surface. The preferred chloramine group is an N-chloroarylsulfonamide, such as N-chlorobenzenesulfonamide.

In using the oxidant described in Ser. No. 311,077, one or more beads can be added to a vessel which contains, in addition to the specimen to be iodinated, buffer and sodium iodide. As with other oxidants, the bead mediates the generation of the iodous ion in situ which is then available to react with the phenolic moiety of tyrosine groups present in the specimen or other groups susceptible to iodination such as histidine. After the desired amount of iodination has occurred, the iodination can be stopped by removing the solution containing the specimen from the vessel with a pipette. Separation of the iodinated specimen from the solution containing residual radioactive species is generally accomplished by acid precipitation or gel filtration.

There are several advantages of using the above described oxidant. It is completely water insoluble and can function in almost any iodinating medium. It can be easily prepared and with a determinable oxidizing capacity. Moreover, being a head, it is easy to handle thus permitting facile addition to the reaction vessel for initiation of reaction and subsequent separation for termination.

It will, however, be recognized that all of the techniques described above are indirect in that they require, during iodination, the presence of sodium iodide and an independent oxidant in order to generate the iodous ion.

Now, in accordance with the present invention, there is provided an effective direct-acting iodinating reagent which, because it is direct, avoids the necessity of having present at the same time both an oxidizing agent and sodium iodide. The reagent of this invention comprises a conjugate of an iodous ion and a water insoluble support. The manner of conjugation is such that the ion is complexed onto the surface of the support but is still free to react with groups in proteins susceptible to iodination and thus be transferred to the biological specimen being iodinated. As used herein, the term "complexed" means that the association between the iodous ion and the support is not covalent, but is such that the ion and support form an integral unit, which does not readily disassociate in an aqueous medium under mild conditions of pH and temperature. Apart from the advantage of being direct-acting, the reagent has those desirable attributes mentioned above which are associated with water insoluble oxidants as well as other features and advantages which will become apparent as the description proceeds.

One technique for preparing the reagent of this invention involves reacting sodium iodide, in solution, with a water insoluble support which has, covalently attached to its surface, molecules containing a chloramine group, and then removing the support from the solution. The reagent can then be washed and dried. Alternatively, after the reagent has been prepared, the specimen to be iodinated can be added directly to the vessel in which the reagent was prepared.

Particularly useful insoluble supports for reaction with sodium iodide are the beads disclosed as oxidants in Ser. No. 311,077. These beads are preferably non-porous and, as the chloramine group, have a N-chloroarylsulfonamide group such as N-chlorobenzenesulfonamide. As described in Ser. No. 311,077, useful beads can be prepared by chemically treating commercially available beads to modify their surfaces to contain chloramine groups. For example, if nylon beads are employed, N-chlorosulfonamide groups can be created by reacting endogenous and/or derived amine groups on the bead surface with benzene di-sulfonyl chloride followed by treatment with aqueous ammonia and then alkaline hypochlorite solution. The same reaction treatment can be used with beads fashioned from alkylamine substituted ceramic supports such as glass, alumina, silica, etc. With respect to aromatic containing polymers, such as polystyrene, the basic polymer backbone can be used to provide the desired aryl functionality. Thus, sequential treatment of polystyrene with chlorosulfonic acid, aqueous ammonia, and sodium hypochlorite yields the N-chlorobenzenesulfonamide functionality.

Reaction of the insoluble support with sodium iolide to yield the reagent of this invention proceeds readily at room temperture. Preferably, the iodide is dissolved in a buffered aqueous solution at a pH of about 7–8.

Iodinations are frequently done on small samples of biological specimens which may have taken days or weeks to obtain. Therefore, the reagent of this invention preferably has certain physical and chemical characteristics which are designed to avoid specimen loss. One of these is that it be non-porous. With a non-porous bead, the likelihood of loss of specimen being iodinated through entrapment or entrainment within the bead is avoided. A similar consideration governs the selection of the chemical nature of the insoluble support. It should not have surface characteristics which cause an affinity interaction between the specimen and the support. Non-porous beads fashioned from non-ionic polymers such as polystyrene have been found to be very suitable for use in this invention as the insoluble support.

The size of the support is an important parameter. It must be large enough so that it can be handled in a manner such that a known quantity of the reagent can be contacted with the biological specimen and such that an easy separation of the specimen from the reagent can be achieved. Where the insoluble support is a bead, those of a size which can be individually handled with tweezers and which have dimensions such that they cannot be drawn up with iodinated specimen by, for example, an 18 gauge syringe needle, are useful.

The maximum size of the insoluble support is influenced by the size of the sample to be iodinated and, if beads are employed, by how many beads are to be used at once. For iodinating efficiency, the support should be covered by the specimen being iodinated and, for a given volume of reagent in the form of beads, greater capacity is obtained by using more, smaller beads rather than fewer, larger beads. So that a small quantity of reagent can be employed for most iodinations, iodinating capacity should be at least 1 $\mu$eq/in$^2$ of support surface area and, preferably, at least 10 $\mu$eq/inch$^2$. As used in this invention, the iodinating capacity of the reagent is equivalent to the oxidating capacity of the insoluble support from which it is prepared. While shape is not especially important, useful reagents can be prepared from insoluble supports in the form of spherical beads having diameters of about 0.01 inch to about 0.25 inch.

Though actual size and shape of the support are not especially critical, it is preferred that size, shape, and chloramine group content be reproducible so that a plurality of supports with substantially identical size, shape, and chloramine content can be obtained. In turn, by reacting at one time a number of such supports with sodium iodide, reagents with the same iodinating capacity will be obtained. And, by using one or, in the case of beads, several of the supports in a controlled iodinating experiment, the capacity of those reagents and, in turn, each of the reagents in the batch can be determined. Where supports of different sizes or shapes are treated at once, or the supports are porous, then actual capacity is not as easily determinable since surface area of both the reagent used in the control and of that used in the iodination must be measured or approximated.

Example I illustrates the preparation of a water insoluble support useful in preparing reagent of this invention.

EXAMPLE I

About 500 commercially available (Clifton Plastics, Clifton Heights, PA) non-crosslinked, non-porous polystyrene spherical beads (0.125 inch diameter) were placed in a flask containing 25 ml of chlorosulfonic acid (100%). After about three minutes, excess acid was drained off and the beads quenched in 200 ml ice and 100 ml water and then washed with water at a temperature just above freezing. Then, the beads were transferred to a flask containing 100 ml of ice and 100 ml of conc. ammonium hydroxide and, after about five minutes, removed and washed with water. Finally, the beads were added to 100 ml of commercial bleach and, after five minutes, washed with a solution of sodium bicarbonate and then blotted dry.

Oxidizing capacity can be determined by measuring how much of a known reductant is removed by a given amount of insoluble support. Accordingly, 20 beads of support prepared as above described are placed in a test tube with 2.00 ml of the reductant sodium thiosulfate (0.0100N, 20 $\mu$eq.) and 2.00 ml of pH 7.4 buffer (0.25 M sodium phosphate). After agitation for 50 minutes in an ultrasonic bath, the beads were removed and the liquid titrated with 0.0100 N. iodine solution to determine the amount of unreacted sodium thiosulfate. 0.89 ml of iodine solution was used (8.9 $\mu$eq. of I$_2$) meaning that 1.11 ml (11.1 $\mu$eq) of thiosulfate was consumed. In turn, this 11.1 $\mu$eq. is the oxidizing capacity of the 20 beads with each bead thus having a capacity of 0.55 $\mu$eq. Based on bead surface area, the oxidizing capacity is 11.2 $\mu$eq/in$^2$. This capacity is maintained for at least 6 months when the beads are refrigerated.

Example II illustrates the use of the insoluble support prepared in Example I for the preparation of iodinating reagent of this invention.

EXAMPLE II 250 beads prepared as in Example I were added to 35 ml of sodium phosphate buffer, 0.25 M, pH 7.4, containing sodium iodide at a concentration of 4,000 nmml. Gentle mixing was continued at room temperature for about 10 minutes, after which time the beads and supernatant had turned yellow. After decanting, the beads were washed with 4-20 ml aliquots (1 minute each wash) of the phosphate buffer, blotted dry, and then placed under a stream of nitrogen for 1 hour. For storage, the reagent can be wrapped in foil and kept at 4° C.

Example III illustrates use of the reagent prepared in Example II for the iodination of the tripeptide Glycine-Tyrosine-Glycine (GTG).

EXAMPLE III

A GTG solution was prepared in the phosphate buffer of Example II to a GTG concentration of 200 nm/ml. To 1 ml aliquots of the solution 3, 4, 5, or 6 beads prepared as in Example II were added and the solutions mixed on a rocker at room temperature for 5, 10, or 15 minutes. After the desired time, iodination was terminated by removing the solution from the reaction vessel with a Pasteur pipette. High performance liquid chromatography (HPLC) was used to determine the degree and manner of iodination. The results are given in Table I.

TABLE I

| # of Beads | Reaction Time (Min) | Mole Percent* | | |
|---|---|---|---|---|
| | | GTG | GTG-I | GTG-I$_2$ |
| 3 | 5 | 67 | 9.6 | 23.5 |
| 3 | 10 | 50 | 13.1 | 36.99 |
| 3 | 15 | 37 | 14.5 | 48.5 |
| 4 | 5 | 56.3 | 11.6 | 32.1 |
| 4 | 10 | 36 | 14.4 | 49.6 |
| 4 | 15 | 24.9 | 14.8 | 59.3 |
| 5 | 5 | 50.5 | 12.9 | 36.6 |
| 5 | 10 | 27.2 | 14.8 | 58.0 |
| 5 | 15 | 15.8 | 13.2 | 71.1 |
| 6 | 5 | 41.6 | 13.8 | 44.6 |
| 6 | 10 | 16.9 | 13.3 | 69.8 |
| 6 | 15 | 6.4 | 8.9 | 84.7 |

*GTG = non-iodinated peptide
GTG-I = iodinated peptide with one iodine on tryosine phenolic ring.
GTG-I$_2$ = iodinated peptide with two iodines on tyrosine phenolic ring.

As illustrated in Table I, one desirable aspect of using the reagent of this invention is the ability, where desired, to achieve the combination of low (e.g., less than 50%) overall iodination of the specimen with, however, more molecules being di-iodinated than mono-iodinated. The ability to achieve this combination is important where high specific activity is required, but where biological activity is diminished or lost if multiple tyrosyl residues in the specimen are iodinated. With systems wherein "in situ" formation of the iodous ion is achieved, the mono-iodinated specie predominates in early stages of the reaction with di-iodination only occurring after a significant amount of the specimen has already been iodinated.

Further advantages accompanying use of this reagent arise from the fact that the radioactive moiety is conjugated to the support. Because of this, free radioactive iodine is minimized in the iodinating vessel. And, as a result, once the iodinated specimen has been withdrawn from the vessel, less cleanup of the specimen is required. Lastly, the reagent can be used under mild conditions thus minimizing the possibility of damage to the specimen. In this respect it should be appreciated that the pressure of an oxidizing agent is not required during the iodination reaction, thus minimizing the possibility of oxidative degradation of the specimen being iodinated.

While the invention has been described with respect to certain embodiments, it is not intended to be limited to those embodiments. On the contrary, the invention embraces all those modifications and alternatives as may be included within the scope of the appended claims.

We claim:

1. The process of making a reagent useful for the direct iodination of a biological specimen comprising reacting, in an aqueous medium, sodium iodide with an oxidant comprised of a water insoluble suppot having covalently attached to its surface molecules containing a chloramine group and recovering the support from said aqueous medium, said reaction being such that iodous ions are complexed onto the support but are free to react with groups susceptible to iodination in proteins and be transferred to the specimen being iodinated.

2. The reagent prepared by the process of claim 1.

3. The reagent of claim 2 wherein the insoluble support is in the form of a non-porous bead having negligible affinity for said specimen and having a size and shape permitting easy physical separation of the reagent from a solution of said biological specimen.

4. The reagent of claim 3 wherein the bead is spherical and has a diameter of about 0.1 inch to about 0.25 inch.

5. The reagent of claim 3, 4, or 2 wherein the bead is polystyrene.

6. The process of claim 1 wherein the oxidant has an oxidizing capacity of at least 1 $\mu$eq/in$^2$ of support surface area.

7. The process of claim 6 wherein the oxidant has an oxidizing capacity of at least 10 $\mu$eq/in$^2$ of support surface area.

8. The process of claim 7 wherein the chloramine group of the oxidant is an N-chloroarylsulfonamide group, the support is a non-porous bead, and the bead has negligible affinity for said biological specimen.

9. The process of claim 1, 6, 7, or 8 wherein the support is polystyrene and the N-chloroarysulfonamide groups are chloramine groups.

10. The use of the reagent of claim 2 in iodinating a biological specimen comprising contacting, in an aqueous medium, said reagent with the biological specimen to be iodinated and then removing said reagent from said aqueous medium.

11. The use of the reagent of claim 2 in iodinating a biological specimen comprising contacting, in an aqueous medium, said reagent with the biological specimen to be iodinated and then removing said reagent from said aqueous medium.

12. The use of the reagent prepared by the process of claim 1 in iodinating a biological specimen comprising contacting, in an aqueous medium, said reagent with the biological specimen to be iodinated and then removing said reagent from said aqueous medium.

13. The reagent prepared by the process of claim 8.

* * * * *